United States Patent [19]

Eto et al.

[11] 4,190,651
[45] Feb. 26, 1980

[54] CYCLIC PHOSPHORIC ACID AMIDE ESTERS, AND AN INSECTICIDE CONTAINING THE SAME AS ACTIVE INGREDIENT

[75] Inventors: Morifusa Eto; Shinkichi Tawata, both of Fukuoka; Kohei Oshima, Tama, all of Japan

[73] Assignee: Kyowa Hakko Kogyo Kabushiki Kaisha, Tokyo, Japan

[21] Appl. No.: 884,527

[22] Filed: Mar. 8, 1978

[30] Foreign Application Priority Data

Mar. 16, 1977 [JP] Japan ................................. 52/29103

[51] Int. Cl.² ........................ C07F 9/08; A01N 9/36
[52] U.S. Cl. ................................. 424/209; 260/936
[58] Field of Search ......................... 260/936; 424/209

[56] References Cited

FOREIGN PATENT DOCUMENTS 763485  12/1956  United Kingdom ..................... 260/936

OTHER PUBLICATIONS

Mukaiyama et al., "Bul. Chem. Soci. Japan", vol. 39, (1966), pp. 1297–1301.
Eto et al., "Abstract of the Lectures on the 1977 Annual Meeting of the Japanese Agricultural Chemistry Society", Mar. 10, 1977, p. 457.

*Primary Examiner*—Anton H. Sutto
*Attorney, Agent, or Firm*—Wolder, Gross & Yavner

[57] ABSTRACT

The present invention relates to novel cyclic phosphoric acid amide esters, a process for producing the same and an insecticide containing the same as active ingredient. The present invention provides novel 4-substituted-1,3,2-oxazaphospholidine derivatives of the general formula:

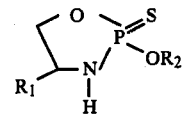

I wherein $R_1$ represents an alkyl, alkenyl, alkynyl, aralkyl, aralkenyl or aralkynyl group and $R_2$ represents an alkyl group. The compounds of the formula I may be produced by the reaction of a compound of the formula:

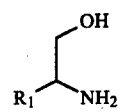

II wherein $R_1$ is as hereinbefore defined or an alcoholate thereof with a compound of the formula:

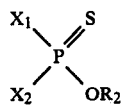

III wherein $R_2$ is as hereinbefore defined and $X_1$ and $X_2$, which may be same or different, each represents an atom or group removable as an anion. The compounds of the formula I have interesting insecticidal activity particularly against houseflies, adzuki-been weevil, mulberry mealy bug etc.

18 Claims, 8 Drawing Figures

CYCLIC PHOSPHORIC ACID AMIDE ESTERS, AND AN INSECTICIDE CONTAINING THE SAME AS ACTIVE INGREDIENT

The present invention relates to novel cyclic phosphoric acid amide esters and to processes for their preparation. These compounds possess interesting insecticidal activity.

Certain cyclic phosphoric acid amide esters have been described in the literature. Thus for example British Patent Specification No. 763 485 describes compounds having insecticidal activity of the formula:

wherein $X_A$ is an oxygen or sulphur atom, $R_A$ is a hydrogen atom or an alkyl group, $R_B$ is an alkyl group and $R_C$ is an alkyl group. The Bulletin of The Chemical Society of Japan, Vol. 39, 1296–1297 (1966) describes a process for producing cyclic phosphoric acid amide esters of formula:

wherein $X_B$ is an oxygen or sulphur atom, $R_D$ is a hydrogen atom or a methyl group and $R_E$ is an alkyl group, but discloses no use for these compounds.

The present invention is based on the discovery that certain novel 4-substituted cyclic phosphoric acid amide esters posess interesting insecticidal activity.

Thus according to one feature of the present invention there are provided compounds of the general formula:

wherein $R_1$ represents an alkyl, alkenyl, alkynyl, aralkyl, aralkenyl or aralkynyl group and $R_2$ represents an alkyl group.

The compounds of the present invention include an asymmetric carbon atom and thus exist in the form of optically active isomers as well as in the form of a racemic mixture. All such forms of the compounds of formula I are included within the scope of the present invention.

The compounds of the present invention possess interesting insecticidal activity and compounds of the invention which have been tested have been found to possess good activity against, for example, houseflies, greenhouse whiteflies, mulberry mealy bugs and adzuki-bean weevils.

Preferred compounds according to the present invention, by virtue of their particularly favourable insecticidal activity, include compounds of formula I wherein $R_1$ represents an alkyl, alkenyl or alkynyl group with not more than 6 carbon atoms, or an aralkyl, aralkenyl or aralkynyl group with 7 to 11 carbon atoms, the aryl moiety of which may optionally be substituted by at least one alkyl or alkoxy group with 1 to 4 carbon atoms or a halogen atom and $R_2$ represents an alkyl group with 1 to 6 carbon atoms. Such preferred compounds include, for example, compounds of formula I wherein $R_1$ represents an alkyl group with 1 to 4 carbon atoms or a benzyl group and $R_2$ represents an alkyl group with 1 to 3 carbon atoms.

Especially preferred compounds according to the present invention by virtue of their especially favourable insecticidal activity include the following:

(4S)-2-Ethoxy-4-methyl-1,3,2-oxazaphospholidine-2-sulphide;
2-Ethoxy-4-ethyl-1,3,2-oxazapholidine-2-sulphide;
(4S)-2-Methoxy-4-isopropyl-1,3,2-oxazaphospholidine-2-sulphide;
(4S)-2-Ethoxy-4-isopropyl-1,3,2-oxazaphospholidine-2-sulphide;
(4S)-2-Ethoxy-4-sec-butyl-1,3,2-oxazaphospholidine-2-sulphide;
(4S)-2-Methoxy-4-isobutyl-1,3,2-oxazaphospholidine-2-sulphide;
(4S)-2-Ethoxy-4-isobutyl-1,3,2-oxazaphospholidine-2-sulphide;
(4S)-2-Ethoxy-4-benzyl-1,3,2-oxazaphospholidine-2-sulphide;
(4R)-2-Methoxy-4-isobutyl-1,3,2-oxazaphospholidine-2-sulphide.

According to a further feature of the present invention there is provided a process for the preparation of compounds of formula I as hereinbefore defined which comprises reacting a compound of the formula:

wherein $R_1$ is as hereinbefore defined or an alcoholate thereof with a compound of the formula:

wherein $R_2$ is as hereinbefore defined and $X_1$ and $X_2$, which may be the same or different, each represents an atom or group removable as an anion whereby a compound of formula I is obtained.

A compound of formula III is advantageously used in which $X_1$ and $X_2$, which may be the same or different, each represents a halogen atom. Preferably a compound of formula III is used in which $X_1$ and $X_2$ each represent a chlorine atom.

The reaction is conveniently effected in the presence of a base, this being especially preferred when a compound of formula II as opposed to the corresponding alcoholate is used.

The process of the present invention is conveniently effected using a compound of formula II in which $R_1$ represents an alkyl group with 1 to 6 carbon atoms or an aralkyl group with 7 to 11 carbon atoms. $R_1$ in the compounds of formula II may be straight and/or branched chain and may include unsaturated bonds. Where $R_1$ in the compound of formula II represents an aralkyl group the aryl moiety e.g. the benzene ring may include alkyl groups having from 1 to 4 carbon atoms, alkoxy groups or halogen atoms as substituents. The alkyl moiety of the aralkyl group may be straight or branched chain, and may also include unsaturated bonds.

Compounds of formula II which may, for example, be employed in the processes of the present invention, depending upon the compound of formula I to be prepared, have the boiling points and specific rotations set out in the following Table 1.

nient to use an anhydrous solvent or a solvent which has been dried. The reaction is preferably effected at a temperature of from $-10°$ to $+10°$ C. In order to keep the reaction temperature below 10° C., the reaction vessel is preferably cooled with ice. The reaction time is usually from one to three hours. The compound of formula II or the alcoholate thereof is conveniently used in a concentration of from 0.05 to 0.5 mol/liter of the compound used as solvent. An equimolar amount or molar excess e.g. a slight molar excess of the compound of formula III is conveniently used per mole of the com-

TABLE 1

| Compound of the formula [II] | Formula | Boiling or melting point | $[\alpha]_D^{25}$ |
|---|---|---|---|
| (2S)-2-amino-propanol (alaninol) | CH₃-CH(NH₂)-CH₂OH | 65°–67° C./ 10 mmHg | +22.5 (C = 15 in dioxan) |
| (2S)-2-amino-3-methylbutanol (valinol) | (CH₃)₂CH-CH(NH₂)-CH₂OH | 91°–92° C./ 10 mmHg | +14.5 (C = 12 in dioxan) |
| (2S)-2-amino-4-methylpentanol (leucinol) | (CH₃)₂CHCH₂-CH(NH₂)-CH₂OH | 90°–92° C./ 11 mmHg | +3.0 (C = 20 in ethanol) |
| (2S)-2-amino-3-methylpentanol (iso-leucinol) | CH₃CH₂CH(CH₃)-CH(NH₂)-CH₂OH | 108°–109° C./ 13 mmHg | −3.5 (C = 20 in ethanol) |
| 2-aminobutanol | CH₃CH₂CH(NH₂)CH₂OH | commercial product | racemic compound |
| (2S)-2-amino-3-phenylpropanol (phenylalaninol) | C₆H₅CH₂-CH(NH₂)-CH₂OH | m.p. 90°–91° C. | −25.8 (C = 10 in ethanol) |
| (2R)-2-amino-4-methylpentanol (D-leucinol) | (CH₃)₂CHCH₂-CH(NH₂)-CH₂OH | 92°–93° C./ 10 mmHg | $[\alpha]_D^{20} = -4.79$ (C = 11.7 in benzene) |

The compound of formula II used in the processes of the present invention may be in optically active or racemic form depending upon the compound of formula I which it is desired to prepare.

A compound of formula III may for example be used in processes of the present invention in which $R_2$ represents a methyl, ethyl or propyl group depending upon the compound of formula I which it is desired to prepare.

Bases which may conveniently be used in the processes of the present invention include organic bases e.g. tertiary organic bases such as triethylamine and pyridine. Where the base employed is a liquid the base may, if desired, additionally serve as the solvent.

The reaction is conveniently effected in the presence of an inert solvent which thus does not react with the starting compounds and may be used either along or in combination with other inert solvents as the solvent for the reaction. Preferred organic solvents include dioxan, benzene, toluene, xylene or chloroform. In order to avoid side reactions it is advantageous to conduct the reaction in the absence of water and it is thus convepound of formula III or the alcoholate thereof. 2 to 2.2 Mols of base are preferably used per mole of the compound of formula II or alcoholate thereof.

In a preferred embodiment of the process of the present invention the reaction is conducted by dissolving the alkylphosphorodichlorido thionate of formula III in a reaction solvent and adding the solution thus obtained to the reaction vessel. Then the aminoalcohol of formula II and the base, both dissolved in a reaction solvent, are added dropwise with agitation to the mixture in the reaction vessel. It is possible if desired to reverse the order of the addition. The reaction product obtained is isolated from the reaction mixture and purified in the following manner:-

After completion of the reaction, the salt formed with hydrogen chloride and the base is separated out from the reaction mixture by filtration. The filtrate is concentrated, followed by evaporation under reduced pressure or by column-chromatography. In this manner, the desired product is isolated and purified. Certain products obtained by this method and their physical properties are shown in Table 2.

TABLE 2

| Compound No. | Name | Substituents in formula [I] R₁ | R₂ | Boiling point(°C.) | $[\alpha]_D^{25}$ |
|---|---|---|---|---|---|
| 1. | (4S)-2-ethoxy-4-methyl-1,3,2-oxazaphospholidine-2-sulphide | $CH_3-$ | $C_2H_5$ | 105–107/0.05 mmHg | +15.20 (C = 5 in ethanol) |
| 2. | 2-ethoxy-4-ethyl-1,3,2-oxazaphospholidine-2-sulphide | $C_2H_5-$ | $C_2H_5$ | 105–106/0.005 mmHg | racemic compound |
| 3. | (4S)-2-methoxy-4-isopropyl-1,3,2-oxazaphospholidine-2-sulphide | $(CH_3)_2CH-$ | $CH_3$ | 107–108/0.006 mmHg | not measured |
| 4. | (4S)-2-ethoxy-4-isopropyl-1,3,2-oxazaphospholidine-2-sulphide | $(CH_3)_2CH-$ | $C_2H_5$ | 110–111/0.04 mmHg | −8.12 (C = 5 in ethanol) |
| 5. | (4S)-2-ethoxy-4-sec-butyl-1,3,2-oxazaphospholidine-2-sulphide | $CH_3-CH_2-CH(CH_3)-$ | $C_2H_5$ | 123–124/0.05 mmHg | −3.46 (C = 5 in ethanol) |
| 6. | (4S)-2-methoxy-4-isobutyl-1,3,2-oxazaphospholidine-2-sulphide | $(CH_3)_2CH-CH_2-$ | $CH_3$ | 115–116/0.03 mmHg | +1.22 (C = 5 in ethanol) |
| 7. | (4S)-2-ethoxy-4-isobutyl-1,3,2-oxazaphospholidine-2-sulphide | $(CH_3)_2CH-CH_2-$ | $C_2H_5$ | 120–121/0.05 mmHg | −4.73 (C = 20 in ethanol) |
| 8. | (4S)-2-ethoxy-4-benzyl-1,3,2-oxazaphospholidine-2-sulphide | $C_6H_5-CH_2-$ | $C_2H_5$ | not measured | −15.14 (C = 5 in ethanol) |
| 9. | (4R)-2-methoxy-4-isobutyl-1,3,2-oxazaphospholidine-2-sulphide | $(CH_3)_2CH-CH_2-$ | $CH_3$ | 115–116/0.03 mmHg | not measured |

Insectcidal experiments were carried out by using as test insects, houseflies (*Musca domestica vicina*) of various strains such as for example Takatsuki-strain, Misaki-strain etc., adzuki-bean weevil (*Callosobruchus chinensis*), greenhouse whitefly (*Trialeudes vaporariorum*) and mulberry mealy bug (*Pseudococcus comstocki*).

In these experiments, Sumithion [fenitrothion viz. dimethyl-(3-methyl-4-nitrophenyl)-thiophosphate; commercially available from Sumitomo Kagaku Kogyo K.K., Japan], salithion [2-methoxy-4H-1.3.2-benzodioxaphosphorine-2-sulphide] and diazinon [O,O-diethyl O-(2-isopropyl-4-methyl-6-pyrimidinyl)-phosphorothionate], which all possess insecticidal activity were used for comparative purposes. A control containing no active ingredient was also used.

As a result of these tests, it can be seen that 4-substituted-1,3,2-oxazaphospholidine derivatives according to the present invention possess interesting insecticidal activity.

(A) Insecticidal experiments using houseflies:

(A-1) Mortality by topical application method:

Adults of houseflies (female) of the Takatuski strain were treated with individual insecticidal samples by conventional topical application, after 3–5 days from emergence. The activity was evaluated by mortality measured after 24 hours from the application. For comparison, Sumithion was used to give the results shown in Table 3.

TABLE 3

| Compound No. | Insecticidal activity against housefly Applied amount (μg/one female) | | | | | | |
|---|---|---|---|---|---|---|---|
| | 100 | 10 | 5 | 1 | 0.5 | 0.1 | 0.05 |
| 1 | 100 | 100 | 70 | 0 | 0 | 0 | 0 |
| 2 | 100 | 100 | 100 | 10 | 0 | 0 | 0 |
| 3 | 100 | 100 | 100 | 100 | 100 | 60 | 20 |
| 4 | 100 | 100 | 100 | 80 | 20 | 0 | 0 |
| 5 | 100 | 100 | 100 | 100 | 20 | 0 | 0 |
| 6 | 100 | 100 | 100 | 100 | 100 | 10 | 0 |
| 7 | 100 | 100 | 100 | 90 | 50 | 0 | 0 |
| 8 | 100 | 100 | 20 | 10 | 0 | 0 | 0 |
| 9* | 100 | 100 | 100 | 100 | 100 | 80 | 10 |
| 10** | 0 | 0 | 0 | 0 | 0 | 0 | 0 |

Notes:
*Sumithion
**Control (A-2) LD₅₀:

Adults of female houseflies of the Takatsuki strain and the Misaki strain were topically treated after 3–5 days from emergence, with individual samples in conventional manner. After 24 hours from the application, the $LD_{50}$ was determined and the results are shown in Table 4. Sumithion was used for comparative purposes.

(A-3) KT₅₀ (Median knock-down time):

Adults of female houseflies of the Takatsuki strain and the Misaki strain were treated with individual samples, after 3–5 days from emergence, by placing them in contact with a film formed with a residual sample (200 μg) in a cup in conventional manner (the so called dry film method). Median knock-down time (50%) was measured, as shown in Table 4. Sumithion was again used for comparison purposes.

TABLE 4

Insecticidal activity against housefly

| Compound No. | Housefly Takatsuki-strain LD$_{50}$ (μg/female) | KT$_{50}$ (min) | Misaki-strain LD$_{50}$ (μg/female) | KT$_{50}$ (min) |
|---|---|---|---|---|
| 1 | 16 | 60 | 3.5 | — |
| 2 | 1.5 | 41 | ** | — |
| 3 | 0.16 | 20 | 0.14 | 11.5 |
| 4 | 1.2 | 37.5 | 0.68 | — |
| 5 | 1.07 | 39 | 1.2 | — |
| 6 | 0.23 | 18 | 0.29 | 12 |
| 7 | 1.00 | 31 | 1.12 | 15 |
| 8 | 2.16 | >200 | 2.35 | — |
| 9 | — | — | 1.06 | — |
| 10* | 0.09 | 22 | 10.03 | >240 |

Notes:
*Sumithion
**100% at 30 μg/female (A-4) Insecticidal activity against houseflies of various strains:

Adults of female houseflies of various strains shown in Table 5 were topically treated with individual samples in conventional manner after 3–5 days from emergence to give the results shown in Table 5. LD$_{50}$ (μg/female) was determined after 24 hours from the application. For comparative purposes, Sumithion and diazinon were used.

TABLE 5

Insecticidal activities against houseflies of various strains [LD$_{50}$ (μg/female)]

| Compound No. | Lab-em-7em | Yuzawa | Yasato | Daisan-Yumeno-shima |
|---|---|---|---|---|
| 3 | 0.066 | 0.513 | 0.892 | 1.225 |
| 6 | 0.085 | 0.407 | 0.585 | 0.964 |
| Diazinon | 0.02 | 0.268 | 1.600 | 12.110 |
| Sumithion | 0.03 | — | — | 11.98 |

(B) Insecticidal experiment using adzuki-bean weevil:

Adults of the female adzuki-bean weevil were treated with individual samples after one day from emergence by the conventional dry film method. The mortality was determined after 24 hours from treatment, as shown in Table 6. For comparison, Sumithion was used.

TABLE 6

Insecticidal activity against adzuki-bean weevil

| Compound No. | Residual amount (μg/cup) 25 | 10 | 5 | 2.5 | 1 | 0.5 |
|---|---|---|---|---|---|---|
| 1 | 100 | 100 | 20 | 0 | 0 | 0 |
| 2 | 100 | 100 | 50 | 10 | 0 | 0 |
| 3 | 100 | 100 | 100 | 100 | 100 | 30 |
| 4 | 100 | 100 | 100 | 100 | 10 | 0 |
| 5 | 100 | 100 | 50 | 20 | 0 | 0 |
| 6 | 100 | 100 | 100 | 75 | 0 | 0 |
| 7 | 80 | 60 | 5 | 0 | 0 | 0 |
| 8 | 90 | 20 | 0 | 0 | 0 | 0 |
| 9* | 100 | 100 | 100 | 100 | 100 | 20 |
| 10** | 0 | 0 | 0 | 0 | 0 | 0 |

Notes:
*Sumithion
**Control (C) Insecticidal experiment using greenhouse whitefly:

Fifty to sixty adult greenhouse whiteflies were made parasitic on the leaves of kidney-bean seedlings planted in a pot (diameter 15 cm) in a greenhouse. A test sample of a 25% emulsifiable concentrate was prepared by mixing compound No. 7 (25 parts by weight), dimethylformamide (20 parts by weight), cyclohexane (35 parts by weight) and Solpol (20 parts by weight; emulsifier commercially available from Toho Kagaku Kogyo K.K., Japan) and was then diluted with water to give a concentration of 250 ppm. A 50% emulsifiable concentrate of Sumithion and a 25% emulsifiable concentrate of Salithion were also prepared and diluted with water to give a 250 ppm concentration for comparison. The leaves of the seedlings were thoroughly sprayed with individual solutions to wet the leaves and were then allowed to stand for 24 hours. After this, mortality was determined, as shown in Table 7.

TABLE 7

Insecticidal activity against greenhouse whitefly

| Active ingredient | Concentration (ppm) | Mortality (%) |
|---|---|---|
| Compound No. 7 | 250 | 98 |
| Sumithion | 250 | 65 |
| Salithion | 250 | 100 |

(D) Insecticidal activity against mulberry mealy bug:

Each of compounds 3 and 6 (each 25 parts by weight) were mixed with dimethylformamide (20 parts by weight), cyclohexane (35 parts by weight) and Solpol (20 parts by weight) to form the 25% emulsifiable concentrates, each of which was then diluted with water to give a concentration of 500 ppm. For comparison purposes, a wettable powder of salithion (36% by weight/weight) was diluted with water to give a concentration of 360 ppm.

The diluted samples were individually sprayed over the whole bodies of larvae (3rd to 4th instar) of mulberry mealy bug (*Pseudococcus comstocki*) which were then allowed to stand at ambient temperature. Mortality was determined after 3 days from application to give the results shown in Table 8.

TABLE 8

Insecticidal activity against mulberry mealy bugs

| | Concentration (ppm) | Numbers of test mealy bugs | Mortality (%) |
|---|---|---|---|
| Compound 3 | 500 | 248 | 97.6 |
| Compound 6 | 500 | 227 | 94.7 |
| Salithion | 360 | 261 | 99.2 |
| Untreated | 0 | 127 | 5.5 |

According to a still further feature of the present invention there are provided insecticidal compositions comprising as active ingredient at least one compound of formula I as hereinbefore defined in association with an inert carrier or diluent.

The compounds according to the present invention may, if desired, be applied directly to the soil for insecticidal purposes, although it is possible to form insecticidal compositions by mixing the compounds with conventionally used carriers. Insecticidal compositions in the form of powders, wettable powders, emulsifiable concentrates, granules and the like may be produced by combining the compounds with, for example, carriers in the form of liquids or solids such as surfactants, dispersing agents, wetting agents and the like used for agricultural compositions.

Examples of solid carriers include talc, clay, kaolin, diatomaceous earth, white carbon, polyvinylalcohol, wood powder and the like, while preferred liquid carriers are exemplified by water, acetone, acetonitrile, toluene, xylene, methylphthalene and various other solvents conventionally used for the preparation of agricultural compositions.

According to a yet still further feature of the present invention there is provided a method of preventing or inhibiting the growth or proliferation of insects which comprises applying to a site infested with or susceptible to infestation by insects an effective amount of a compound of formula I as hereinbefore defined.

In use for this purpose, the composition of the present invention contains, preferably, from 0.01 to 1% by weight of active ingredient.

The following non-limitative examples illustrate the invention.

EXAMPLE 1

(4S)-2-Ethoxy-4-isobutyl-1,3,2-oxazaphospholidine-2-sulphide

Ethyl-phosphorodichlorido-thionate (3.56 g; 0.02 mol) and dried dioxan (200 ml) were poured into a reaction vessel. Separately, L-leucinol [(2S)-2-amino-4-methylpentanol] (2.34 g; 0.02 mol) and triethylamine (4 g; 0.04 mol) were dissolved in dried dioxan (200 ml) which was then added dropwise to the solution in the reaction vessel over a period of about 5 minutes with agitation. The agitation was further continued for about 10 minutes and then an exothermic reaction was observed. The reaction temperature was kept at a temperature below 10° C. by cooling with ice. The reaction time was about three hours. After the completion of the reaction, the triethylamine hydrochloride formed was removed by filtration, and dioxan was also removed by concentration and filtration. The residual solution was evaporated under reduced pressure to isolate an oily substance (colourless and transparent) in a yield of 56.8%. [In the Examples, the yields were calculated on the basis of the amount of aminoalcohol used.]

Boiling point: 120°–121° C./0.05 mmHg.

$[\alpha]_D^{25} = -4.73$ (C=20 in ethanol).

| Elementary analysis (%): | C | H | N |
|---|---|---|---|
| Found | 43.00 | 8.45 | 6.32 |
| Calculated as $C_8H_{18}NO_2SP$ | 43.03 | 8.13 | 6.27 |

Molecular weight: 223 (by mass-spectrometry).

Infrared absorption spectrum (cm$^{-1}$) by KBr method: 3400, 2950, 1470, 1390, 1370, 1290, 1220, 1140, 1070-980, 950, 900 and 840-670.

Figure 1A:
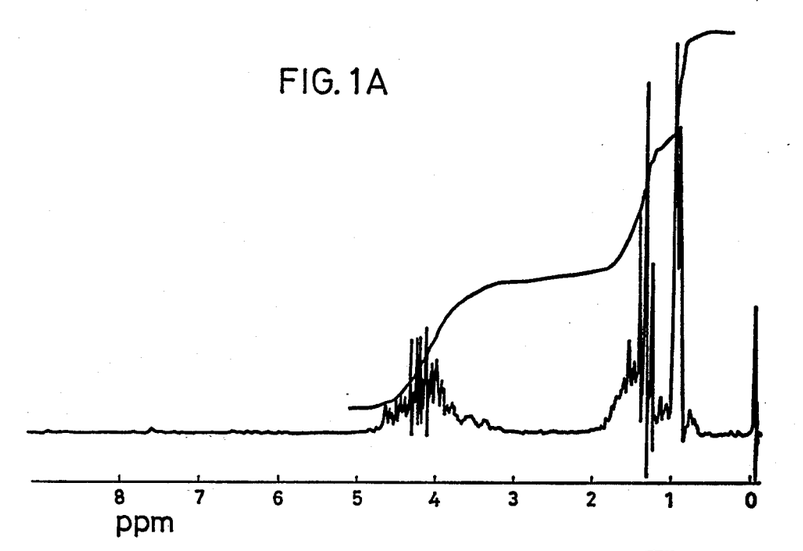

NMR spectrum: shown in FIG. 1A.

The oily substance thus obtained was identified, using this data, as (4S)-2-ethoxy-4-isobutyl-1,3,2-oxazaphospholidine-2-sulphide viz. a compound of the formula [1] wherein $R_1$ = an isobutyl group and $R_2$ = an ethyl group.

EXAMPLE 2

(4S)-2-Ethoxy-4-methyl-1,3,2-oxazaphospholidine-2-sulphide

A similar procedure to that described in Example 1 was carried out with the exception that L-alaninol (1.5 g; 0.02 mol) was used instead of L-leucinol. An oily substance was obtained in a yield of 44.2%.

Boiling point: 105°–107° C./0.05 mmHg.

$[\alpha]_D^{25} = +15.20$ (C=5.0 in ethanol).

| Elementary analysis (%): | C | H | N |
|---|---|---|---|
| Found | 33.11 | 6.84 | 7.76 |
| Calculated as $C_2H_{12}NO_2SP$ | 33.14 | 6.68 | 7.73 |

Molecular weight: 181 (by mass-spectrometry).

Infrared absorption spectrum (cm$^{-1}$) by KBr method: 3400, 2950, 1470, 1390, 1330, 1290, 1210, 1140, 1070-980, 850, 900, 850-700.

Figure 1B:
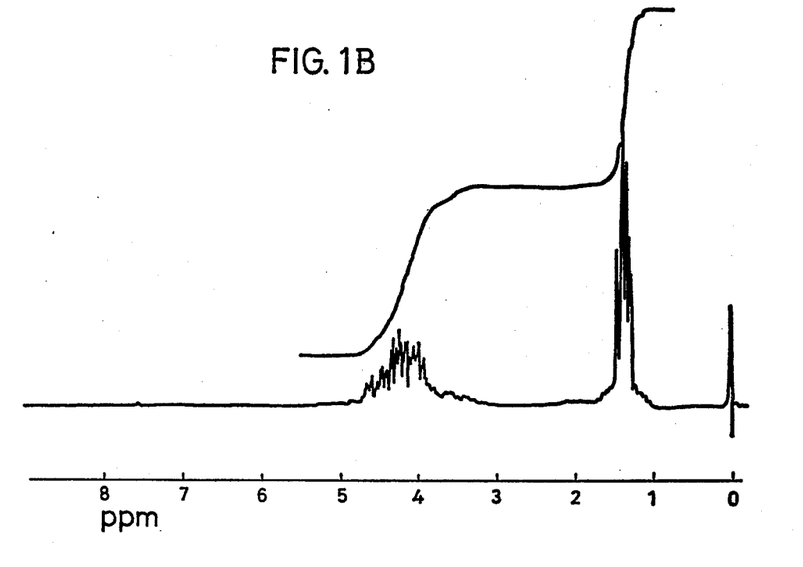

NMR spectrum: shown in FIG. 1B.

The oily substance thus obtained was identified, using the above data, as (4S)-2-ethoxy-4-methyl-1,3,2-oxazaphospholidine-2-sulphide viz. a compound of the formula [1] wherein $R_1$ = a methyl group and $R_2$ = an ethyl group.

EXAMPLE 3

2-Ethoxy-4-ethyl-1,3,2-oxazaphospholidine-2-sulphide

A similar procedure to that described in Example 1 was carried out with the exception that DL-$\beta$-aminobutanol (1.78 g; 0.02 mol) was used instead of L-leucinol. An oily substance (boiling point: 105°–106° C./0.005 mmHg) was obtained.

Yield: 12.8%.

| Elementary analysis (%): | C | H | N |
|---|---|---|---|
| Found | 37.03 | 7.03 | 7.16 |
| Calculated as $C_6H_{14}NO_2SP$ | 36.92 | 7.23 | 7.17 |

Molecular weight; 195.

Infrared absorption spectrum (cm$^{-1}$) by KBr method: 3400, 2950, 1470, 1390, 1310, 1290, 1140, 1070-960, 840-700

Figure 2A:
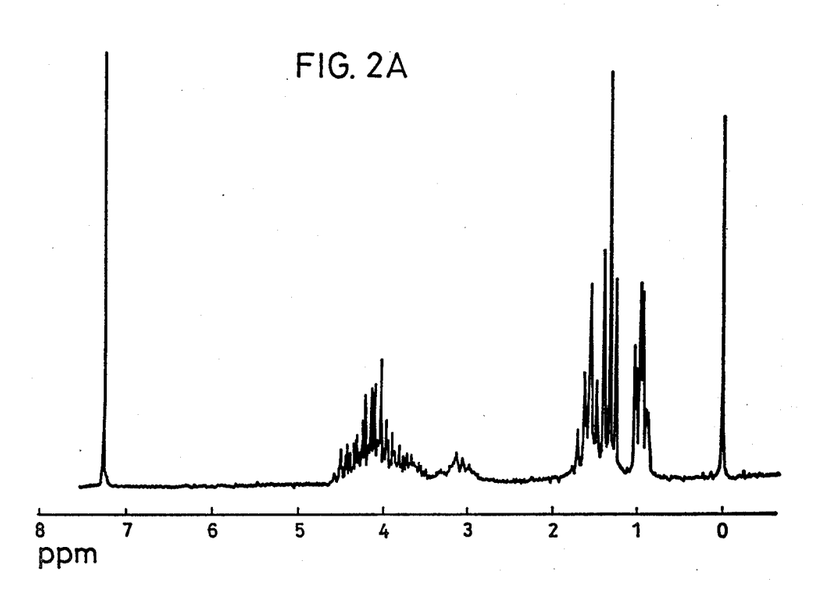

NMR spectrum: shown in FIG. 2A.

The oily substance thus obtained was identified, using the above data, as 2-ethoxy-4-ethyl-1,3,2-oxazaphospholidine-2-sulphide viz. a compound of the formula [1] wherein $R_1$ = an ethyl group and $R_2$ = an ethyl group.

EXAMPLE 4

(4S)-2-Methoxy-4-isopropyl-1,3,2-oxazaphospholidine-2-sulphide

The similar procedure to that described in Example 1 was carried out with the exception that L-valinol (2.06 g; 0.02 mol) was used instead of L-leucinol and that ethylphosphorodichlorido-thionate was replaced with methylphosphorodichlorido-thionate (3.28 g; 0.02 mol). An oily substance was obtained (boiling point: 107°–108° C./0.006 mmHg) in a yield of 10.5%.

Molecular weight: 195.

| Elementary analysis (%): | C | H | N |
|---|---|---|---|
| Found | 35.89 | 7.09 | 6.83 |
| Calculated as $C_6H_{14}NO_2SP$ | 36.92 | 7.23 | 7.17 |

Infrared absorption spectrum (cm$^{-1}$) by KBr method: 3400, 2950, 1470, 1390, 1370, 1310, 1290, 1180, 1140, 1070-980, 920, 900, 840-690.

Figure 2B:
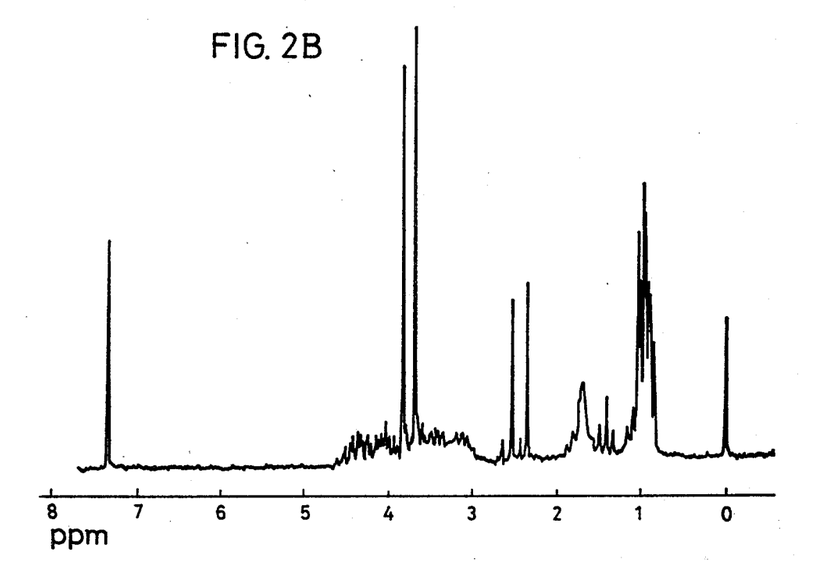

NMR spectrum: shown in FIG. 2B.

The oily substance thus obtained was identified, using the above data, as (4S)-2-methoxy-4-isopropyl-1,3,2-oxazaphospholidine-2-sulphide.

EXAMPLE 5

(4S)-2-Ethoxy-4-isopropyl-1,3,2-oxazaphospholidine-2-sulphide

A similar procedure to that described in Example 1 was carried out with the exception that L-valinol (2.06 g; 0.02 mol) was used instead of L-leucinol. An oily substance was obtained in a yield of 57.4%.

Boiling point: 110°–111° C./0.04 mmHg.
$[\alpha]_D^{25} = -8.12$ (C=5.0 in ethanol).

| Elementary analysis (%): | C | H | N |
|---|---|---|---|
| Found | 39.90 | 7.87 | 6.66 |
| Calculated as $C_7H_{16}NO_2SP$ | 40.18 | 7.71 | 6.69 |

Molecular weight: 209.

Infrared absorption spectrum (cm$^{-1}$) by KBr method: 3400, 2950, 1470, 1390, 1370, 1270, 1140, 1070-980, 950, 840-690.

Figure 3A:
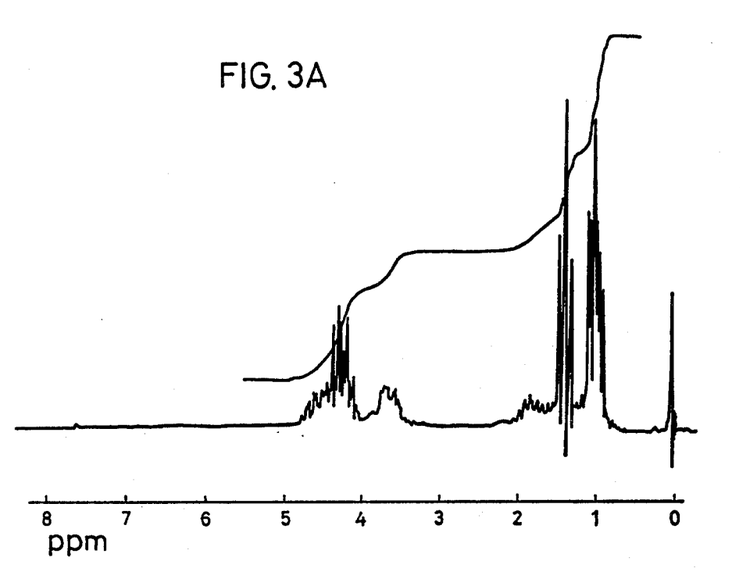

NMR spectrum: shown in FIG. 3A.

The oily substance thus obtained was identified, using the above data, as (4S)-2-ethoxy-4-isopropyl-1,3,2-oxazaphospholidine-2-sulphide.

EXAMPLE 6

(4S)-2-Ethoxy-4-sec-butyl-1,3,2-oxazaphospholidine-2-sulphide

A similar treatment to that described in Example 1 was carried out with the exception that L-isoleucinol (2.34 g; 0.02 mol) was used instead of L-leucinol. An oily substance was obtained in a yield of 49.3%.

Boiling point: 123°–124° C./0.05 mmHg.
$[\alpha]_D^{25} = -3.46$ (C=5.0 in ethanol).

| Elementary analysis (%): | C | H | N |
|---|---|---|---|
| Found | 42.98 | 8.38 | 6.37 |
| Calculated as $C_8H_{18}NO_2SP$ | 43.03 | 8.13 | 6.27 |

Molecular weight: 223.

Figure 3B:
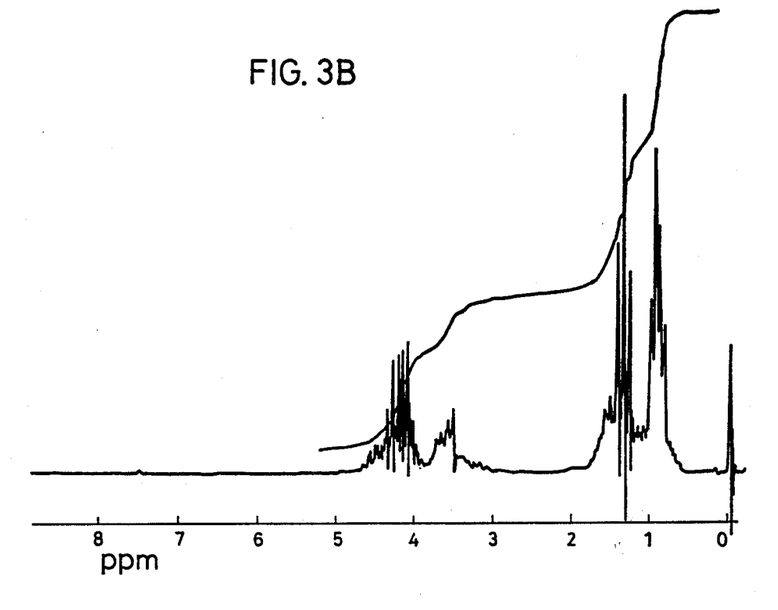

NMR spectrum: shown in FIG. 3B.

The oily substance thus obtained was identified, using the above data, as (4S)-2-ethoxy-4-sec-butyl-1,3,2-oxazaphospholidine-2-sulphide.

EXAMPLE 7

(4S)-2-Methoxy-4-isobutyl-1,3,2-oxazaphospholidine-2-sulphide

A similar treatment to that described in Example 1 was carried out with the exception that methyl-phosphorodichlorido-thionate was used instead of ethyl-phosphorodichlorido-thionate. An oily substance was obtained in a yield of 31.5%.

Boiling point: 115°–116° C./0.03 mmHg.
$[\alpha]_D^{25} = +1.22$ (C=5.0 in ethanol).

| Elementary analysis (%): | C | H | N |
|---|---|---|---|
| Found | 40.21 | 8.08 | 6.72 |
| Calculated as $C_7H_{16}NO_2SP$ | 40.18 | 7.71 | 6.69 |

Molecular weight: 209.

Infrared absorption spectrum (cm$^{-1}$) by KBr method: 3400, 2950, 1470, 1390, 1370, 1340, 1290, 1220, 1180, 1140, 1080-900, 945, 900, and 860-660.

Figure 4A:
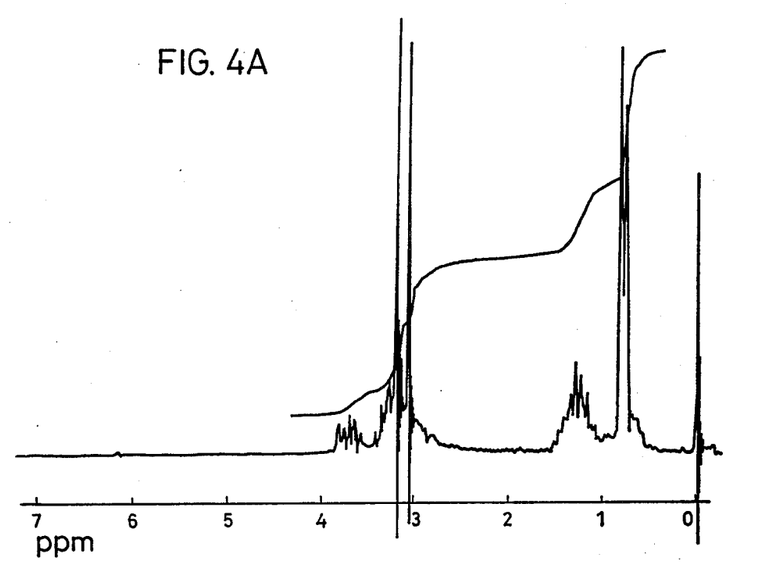

NMR spectrum: shown in FIG. 4A.

The oily substance thus obtained was identified, using the above data, as (4S)-2-methoxy-4-isobutyl-1,3,2-oxazaphospholidine-2-sulphide.

EXAMPLE 8

(4S)-2-Ethoxy-4-benzyl-1,3,2-oxazaphospholidine-2-sulphide

A similar treatment to that described in Example 1 was carried out with the exception that L-phenylalaninol (3.02 g; 0.02 mol) was used instead of L-leucinol. The synthesized material was subjected to column chromatographic treatment to give an oily substance in a yield of 51.4%.

$[\alpha]_D^{25} = -15.14$ (C=5.0 in ethanol).

| Elementary analysis (%): | C | H | N |
|---|---|---|---|
| Found | 50.21 | 6.34 | 5.27 |
| Calculated as $C_{11}H_{16}NO_2SP$ | 51.35 | 6.27 | 5.44 |

Molecular weight: 257.

Figure 4B:
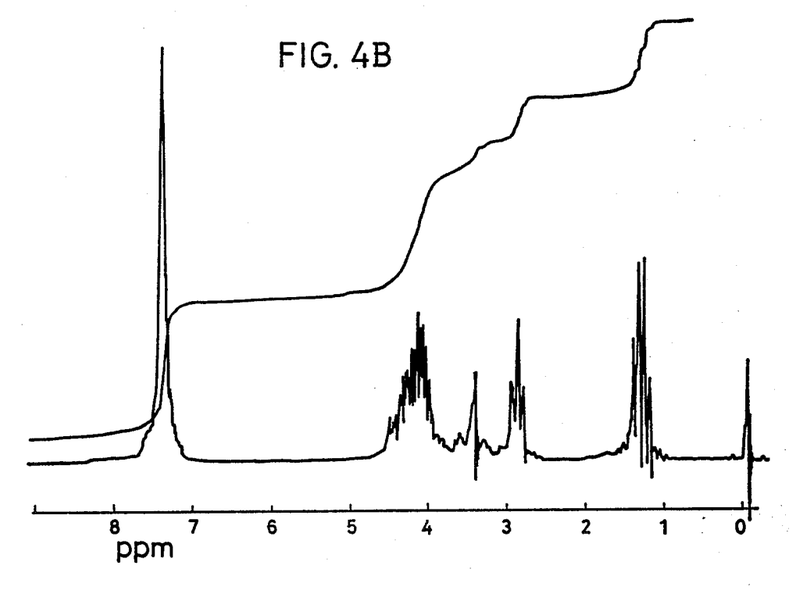

NMR spectrum: shown in FIG. 4B.

The oily substance thus obtained was identified, using the above data, as (4S)-2-ethoxy-4-benzyl-1,3,2-oxazaphospholidine-2-sulphide.

EXAMPLE 9

(4R)-2-Methoxy-4-isobutyl-1,3,2-oxazaphospholidine-2-sulphide

A similar treatment to that described in Example 7 was carried out with the exception that D-leucinol (2.34 g; 0.02 mol) was used instead of L-leucinol. An oily substance was obtained in a yield of 30.0%.

Boiling point: 115°–116° C./0.03 mmHg.

| Elementary analysis (%): | C | H | N |
|---|---|---|---|
| Found | 40.25 | 7.68 | 6.72 |
| Calculated as $C_7H_{16}NO_2SP$ | 40.18 | 7.71 | 6.69 |

Molecular weight: 209

Infrared absorption spectrum (cm$^{-1}$) by KBr method: 3400, 2950, 1470, 1390, 1370, 1290, 1220, 1180, 1140, 1070-980, 945, 900, and 840-670.

The oily substance thus obtained was identified, using the above data, as (4R)-2-methoxy-4-isobutyl-1,3,2-oxazaphospholidine-2-sulphide.

The compounds synthesized in the above-mentioned Examples are new compounds.

Synthesis of aminoalcohols:

The aminoalcohols for use in the preparation of the compounds according to the present invention are known from the literature. For example, the aminoalcohols shown in Table 1 may be produced in a similar manner to that used for the synthesis of L-leucinol, as apparent from the following reference wherein the 2-aminobutanol used was a commercial product.

Reference (Synthesis of L-leucinol)

Thionyl chloride (100 ml) was added dropwise to ice-cooled absolute ethanol (250 ml) which was then stirred at 0° C. for 30 minutes. L-leucine (50 g) was added to the solution and was stirred at ambient temperature for about 24 hours. The reaction was continued until L-leucine was completely dissolved to result in a transparent solution. The solution was concentrated under reduced pressure, and the solid substance thus-formed was recrystallized from ethanol-ether. White needle-like crystals were obtained (melting point: 130°–131° C.) representing L-leucine ethyl ester (hydrochloride). Yield 95%.

L-leucine ethyl ester hydrochloride (40 g; 0.26 mol) was dissolved in 75% ethanol (600 ml), which was added dropwise to a 75% ethanol solution (600 ml) of sodium borohydride [NaBH$_4$ (38 g; 0.1 mol)]. This reaction mixture was allowed to stand at ambient temperature until the generation of hydrogen gas became weak. After this, the solution was boiled under reflux for 5 hours in a water bath. Ethanol was distilled off under reduced pressure, and the resultant aqueous solution was extracted with ethyl acetate. The obtained extract was washed with a saturated sodium chloride solution and was dried by using anhydrous Na$_2$SO$_4$. After removal of ethyl acetate, the solution was concentrated under reduced pressure to give a colourless liquid representing L-leucinol (boiling point: 90°–92° C./11 mmHg) in a yield of 59.6%.

BRIEF DESCRIPTION OF DRAWINGS

FIGS. 1A–4B show NMR spectra of the following compounds.

FIG. 1A (4S)-2-ethoxy-4-isobutyl-1,3,2-oxazaphospholidine-2-sulphide

FIG. 1B (4S)-2-ethoxy-4-methyl-1,3,2-oxazaphospholidine-2-sulphide

FIG. 2A 2-Ethoxy-4-ethyl-1,3,2-oxazaphospholidine-2-sulphide

FIG. 2B (4S)-2-methoxy-4-isopropyl-1,3,2-oxazaphospholidine-2-sulphide

FIG. 3A 2-Ethoxy-4-isopropyl-1,3,2-oxazaphospholidine-2-sulphide

FIG. 3B (4S)-2-ethoxy-4-sec-butyl-1,3,2-oxazaphospholidine-2-sulphide

FIG. 4A (4S)-2-methoxy-4-isobutyl-1,3,2-oxazaphospholidine-2-sulphide

FIG. 4B (4S)-2-ethoxy-4-benzyl-1,3,2-oxazaphospholidine-2-sulphide

FORMULATION EXAMPLES

EXAMPLE A

Emulsifiable Concentrate 25 parts by weight of (4S)-2-methoxy-4-isopropyl-1,3,2-oxazaphospholidine-2-sulphide was mixed with 20 parts by weight of dimethylformamide, 35 parts by weight of cyclohexane and 20 parts by weight of Solpol to form a 25% emulsifiable concentrate.

The emulsifiable concentrate was then diluted with water to give a composition ready for use having an active ingredient concentration of 500 p.p.m.

EXAMPLE B

Emulsifiable Concentrate 25 parts by weight of (4S)-2-methoxy-4-isobutyl-1,3,2-oxazaphospholidine-2-sulphide was mixed with 20 parts by weight of dimethylformamide, 35 parts by weight of cyclohexane and 20 parts by weight of Solpol to form a 25% emulsifiable concentrate.

The emulsifiable concentrate was then diluted with water to give a composition ready for use having an active ingredient concentration of 500 p.p.m.

EXAMPLE C

Emulsifiable Concentrate 25 parts by weight of (4S)-2-ethoxy-4-isobutyl-1,3,2-oxazaphospholidine-2-sulphide was mixed with 20 parts by weight of dimethylformamide, 35 parts by weight of cyclohexane and 20 parts by weight of Solpol to form a 25% emulsifiable concentrate.

The emulsifiable concentrate was then diluted with water to give a composition ready for use having an active ingredient concentration of 250 p.p.m.

We claim:

1. Compounds of the general formula:

wherein $R_1$ is one member selected from the class consisting of alkyl, alkenyl, alkynyl, aralkyl, aralkenyl and aralkynyl groups and $R_2$ is an alkyl group.

2. Compounds of claim 1 wherein $R_1$ is one member selected from the class consisting of alkyl, alkenyl and alkynyl groups, each having not more than 6 carbon atoms, and aralkyl, aralkenyl and aralkynyl groups, each having carbon atoms of 7 to 11, the aryl moiety of which may optionally be substitued by at least one member selected from the class consisting of alkyl and alkoxy groups, each having carbon atoms of from 1 to 4, and a halogen atom and $R_2$ represents an alkyl group with 1 to 6 carbon atoms.

3. Compunds of claim 1 wherein $R_1$ represents one member selected from the class consisting of an alkyl group with 1 to 4 carbon atoms and a benzyl group and $R_2$ represents an alkyl group with 1 to 3 carbon atoms.

4. Compounds of claim 1 in the form of an optically active isomer.

5. A method of preventing or inhibiting the growth of proliferation of insects which comprises applying to a site infested with or susceptible to infestation by insects an effective amount of a compound of formula I as defined in claim 1.

6. Compound of the general formula:

wherein $R_1$ represents one member selected from the class consisting of alkyl, alkenyl and alkynyl groups, each having not more than 6 carbon atoms, and aralkyl, aralkenyl and aralkynyl groups, each having 7 to 11 carbon atoms, the aryl moiety of which may optionally be substituted by at least one member selected from the class consisting of alkyl and alkoxy groups, each having 1 to 4 carbon atoms, and a halogen atom and $R_2$ represents an alkyl group with 1 to 6 carbon atoms.

7. (4S)-2-Ethoxy-4-methyl-1,3,2-oxazaphospholidine-2-sulphide.

8. 2-Ethoxy-4-ethyl-1,3,2-oxazaphospholidine-2-sulphide.

9. (4S)-2-Methoxy-4-isopropyl-1,3,2-oxazaphospholidine-2-sulphide.

10. (4S)-2-Ethoxy-4-isopropyl-1,3,2-oxazaphospholidine-2-sulphide.

11. (4S)-2-Ethoxy-4-sec-butyl-1,3,2-oxazaphospholidine-2-sulphide.

12. (4S)-2-Methoxy-4-isobutyl-1,3,2-oxazaphospholidine-2-sulphide.

13. (4S)-2-Ethoxy-4-isobutyl-1,3,2-oxazaphospholidine-2-sulphide.

14. (4S)-2-Ethoxy-4-benzyl-1,3,2-oxazaphospholidine-2-sulphide.

15. (4R)-2-Methoxy-4-isobutyl-1,3,2-oxazaphospholidine-2-sulphide.

16. Insecticidal compositions comprising as active ingredient at least one compound of the formula I as defined in claim 1 in association with one member selected from an inert carrier and diluent.

17. Compositions of claim 16 in one form selected from powders, wettable powders, emulsifiable concentrates and granules.

18. Compositions of claim 16 containing from 0.01 to 1% by weight of active ingredient.